United States Patent [19]

Dubief et al.

[11] Patent Number: 5,208,014

[45] Date of Patent: May 4, 1993

[54] REDUCING COSMETIC COMPOSITION FOR PERMING THE HAIR, CONTAINING CYSTEAMINE AND/OR ITS N-ACETYL DERIVATIVE AND A CATIONIC POLYMER, AND A PROCESS FOR PERMANENT DEFORMATION OF THE HAIR

[75] Inventors: Claude Dubief, Le Chesnay; Christine Dupuis, Paris, both of France

[73] Assignee: L'Oreal, Paris, France

[21] Appl. No.: 624,218

[22] Filed: Dec. 10, 1990

[30] Foreign Application Priority Data

Dec. 8, 1989 [FR] France ............................ 89 16273
Jan. 19, 1990 [FR] France ............................ 90 00637

[51] Int. Cl.$^5$ ............................ A61K 7/09; A61K 7/11
[52] U.S. Cl. ............................ 424/71; 424/70; 424/78.24; 424/78.31; 424/78.37; 424/DIG. 2; 252/188.2
[58] Field of Search ............... 424/70, 71, 78.31, 78.24

[56] References Cited

U.S. PATENT DOCUMENTS 4,349,532  9/1982  Vanderberghe et al. ............ 424/71

FOREIGN PATENT DOCUMENTS 0299764  1/1989  European Pat. Off. .
2114616  8/1983  United Kingdom .

OTHER PUBLICATIONS

Patent Abstracts of Japan, vol. 12, No. 405 (C-539) [3252], Oct. 26, 1988; & JP-A-63 146 808 (KAO Corp.).

*Primary Examiner*—Thurman K. Page
*Assistant Examiner*—Raj Bawa
*Attorney, Agent, or Firm*—Wegner, Cantor, Mueller & Player

[57] ABSTRACT

A reducing cosmetic composition containing an association of a reducing agent and a cationic polymer is described. The reducing agent is cysteamine or one of its salts and/or N-acetylcysteamine, and the cationic polymer is a copolymer of from 45 to 99.5 mole-% of N-vinylpyrrolidone and from 0.5 to 55 mole-% of non-quaternized dialkyl ($C_1$-$C_4$) aminoalkyl ($C_1$-$C_{18}$) acrylate or methacrylate. The composition can be used in a process for permanent deformation of the hair in the cold state.

18 Claims, No Drawings

REDUCING COSMETIC COMPOSITION FOR PERMING THE HAIR, CONTAINING CYSTEAMINE AND/OR ITS N-ACETYL DERIVATIVE AND A CATIONIC POLYMER, AND A PROCESS FOR PERMANENT DEFORMATION OF THE HAIR

This invention relates to a reducing cosmetic composition for permanent deformation of the hair, containing cysteamine and/or its N-acetyl derivative and a cationic polymer, and its use in a process for permanent deformation of the hair.

The classical technique for realizing the permanent deformation of the hair consists, in a first step, of opening the disulfide bridges of the keratin by means of a composition containing a reducing agent (reduction step) and then, preferably after having rinsed the hair, of reconstituting the disulfide bonds in a second step by applying an oxidizing composition to the hair under tension (oxidation step, also called fixation) so as to give the hair the desired final shape. This technique makes it possible to realize either a waving of the hair or an uncurling or uncrimping.

Among the reducing agents making it possible to realize the first step for permanent deformation of the hair, one generally uses mercaptans such as thioglycolic acid thiolactic acid or a mixture of these acids as well as their esters, e.g., the monothioglycolate of glycerol or of glycol.

Moreover, it has also been proposed to use as a reducing agent 2-aminoethanethiol or cysteamine, following the work of Puri et al. (*International Journal of Cosmetic Science* 1, 59-67, 1979).

Since these reducing agents have a deteriorating effect on the hair, it has been recommended to associate them with cationic polymers.

However, it has been observed that the use of a certain number of these cationic polymers, associated with cysteamine, results in reducing compositions that are unstable in the course of time. After various studies on a very large number of these cationic polymers, it has been ascertained in a completely unexpected and surprising way that a particular class of cationic copolymers, with a base of N-vinylpyrrolidone and nonquaternized dialkyl $(C_1-C_4)$ aminoalykl $(C_1C_{18})$ acrylate or methacrylate, leads to compostions that not only are stable but also makes it possible to obtain perms of excellent quality exhibiting, in particular, a good holding power with a curliness that is more durable in the course of time.

Moreover, it has been shown that these reducing compositions are free of odor, which is particularly desirable not only for persons undergoing a hair-perming operation but also for the persons who perform them.

Finally, the reducing compositions according to the invention make it possible to obtain a better effect in treating the tips of the hairs.

The good stability of the reducing compositions according to the invention thus makes it possible to remedy the disadvantages of prior-art compositions which most often had to be created at the time of use by mixing the reducing agent and the cationic polymer, which were packed separately.

This invention thus has as an object a reducing cosmetic composition for realizing a permanent deformation of the hair in the cold state, containing an association of a reducing agent and a cationic polymer, the reducing agent being cysteamine or one of its salts and/or N-acetylcysteamine, and the cationic polymer being a copolymer of from 45 to 99.5 mole-% of N-vinylpyrrolidone and from 0.5 to 55 mole-% of nonquaternized dialkyl $(C_1-C_4)$ aminoalkyl $(C_1-C_{18})$ acrylate or methacrylate.

According to the invention, the reducing agent of the composition is preferably used at a concentration of between 0.1 and 15% by weight, preferably between 3 and 8% by weight, relative to the total weight of the reducing composition.

According to a preferred form, the cysteamine is used in the form of its hydrochloride at a concentration expressed in terms of base cysteamine as indicated above.

Among the cationic copolymers meeting the above definition, it is preferable according to the invention to use the copolymers of from 80 to 99.5 mole-% N-vinylpyrrolidone and from 0.5 to 20 mole-% dimethylaminoethyl methacrylate.

Among the latter, the ones most particularly preferred are the copolymers sold by the GAF Company under the commercial names "Copolymer 845", "Copolymer 937" and "Copolymer 958"; "Copolymer 845" is especially preferred.

The characteristics of these cationic copolymers with a base of N-vinylpyrrolidone and dimethylaminoethyl methacrylate are as follows:

"Copolymer 845"

Mean molecular weight $= 10^6$;

Sold in the form of an aqueous solution at 20% by weight, having a pH of 6 to 8 and a viscosity of 20,000–40,000 cps (Brookfield RV, 20 rpm, #7 spindle at 25° C.).

"Copolymer 937"

Mean molecular weight $= 10^6$;

Sold in the form of an aqueous solution at 20% by weight, having a pH of 4.5 to 6.5 and a viscosity of 30,000 to 70,000 cps (Brookfield RV, 20 rpm, #7 spindle at 25° C.).

"Copolymer 845" and "Copolymer 937" are sold in aqueous solution at 20% by weight, but have different properties due to the fact that the ratio between N-vinylpyrrolidone and dimethyaminoethyl methacrylate is not the same.

"Copolymer 958"

Mean molecular weight $= 10^5$;

Sold in the form of an alcohol solution at 50% by weight, having a pH of 6.2 to 6.8.

In the reducing compositions according to the invention, the concentration of cationic copolymer as defined above is generally between 0.1 and 3% by weight and preferably between 0.5 and 2% (expressed in terms of active substance) relative to the total weight of the reducing composition.

According to a preferred embodiment of the invention, the cysteamine or one of its salts and/or N-acetylcysteamine can be associated with cysteine or N-acetylcysteine, and in that case the latter are present in the composition at a concentration of between 0.1 and 10% by weight and preferably between 1.5 and 8% by weight.

Preferably, the reducing composition also contains at least one surface-active agent (surfactant) of the nonionic, anionic or amphoteric type but preferably of the nonionic type, and more particularly a poly(hydroxypropylether) nonionic surface-active agent.

Among the poly(hydroxypropylether) nonionic surface-active agents, one may note in particular the compounds of formulas (I) to (III) below and/or the compounds prepared according to the processes described in paragraphs (3) and (4):

$$R_1O+C_3H_5(OH)O\}_nH \quad (I)$$

in which:

the divalent unit —$C_3H_5(OH)O$— represents the following structures, taken in mixed form or separately:

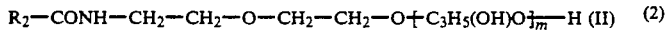

$R_1$ represents an alkyl radical or mixture of alkyl radicals containing from 10 to 14 carbon atoms, and n is a whole or statistical decimal number from 2 to 10, and preferably from 3 to 6.

The particularly preferred compounds of formula (I) above are those in which $R_1$ represents the $C_{12}H_{25}$ radical and n=4.2, or in which $R_1$ represents a mixture of $C_{10}H_{21}$ and $C_{12}H_{25}$ radicals and n=3.75.

These compounds of formula (I) are described in the French patent no. 1,477,048, the disclosure of which is herein incorporated by reference.

$$R_2-CONH-CH_2-CH_2-O-CH_2-CH_2-O+C_3H_5(OH)O\}_m-H \quad (II) \quad (2)$$

in which:

the divalent unit —$C_3H_5(OH)O$— has the same meaning as above for the formula (I), $R_2$ represents an alkyl or alkenyl radical or a mixture of alkyl and/or alkenyl radicals having from 11 to 17 carbon atoms and m designates a whole or statistical-decimal number from 1 to 5, preferably from 1.5 to 4.

Among these compounds of formula (II), the compound having the following formula is particularly preferred:

$$R_2-CONH-CH_2-CH_2-O-CH_2-CH_2-O+C_3H_5(OH)O\}_{3.5}-H$$

in which:

the divalent unit —$C_3H_5(OH)O$— has the same meaning as above for the formula (I), $R_2$ represents a mixture of alkyl or alkenyl radicals chosen among the $C_{11}H_{23}$ or $C_{13}H_{27}$ radicals and the radicals derived from the fatty acids of copra and oleic acid.

These compounds of formula (II) are described more particularly in the French patent no. 76-31975 (2,328,763), the disclosure of which is herein incorporated by reference.

$$R_3-CH-CH_2-O+C_3H_5(OH)O\}_pH \quad (III) \quad (3)$$
$$\phantom{R_3-CH}|$$
$$\phantom{R_3-}O+C_3H_5(OH)O\}_{p'}-H$$

in which:

the divalent unit —$C_3H_5(OH)O$— has the same meaning as above for the formual (I), $R_3$ designates an aliphatic, cycloaliphatic or arylaliphatic radical, preferably having from 7 to 21 carbon atoms, and mixtures thereof, the aliphatic chains representing in particular alkyl chains having from 1 to 6 ether, thioether and/or hydroxymethylene groups, and p+p' is a statistical number from 1 to 10 inclusive.

These compounds are prepared by condensation with alkaline catalysis of from 2 to 10 and preferably from 2.5 to 6 moles of glycidol on an alpha-diol or a mixture of alpha-diols at $C_{10}$–$C_{14}$ at a temperature of 120°–180° C. and preferably from 140° to 160° C.

Preferred according to a particular embodiment are the compounds prepared by condensation with alkaline catalysis of 3.5 moles of glycidol on a mixture of alpha-diols having from 10 to 14 carbon atoms.

These compounds of formula (III) are obtained according to the process described in French patent no. 71-17206 (2,091,516), the disclosure of which is herein incorporated by reference.

(4) Compounds prepared by condensation, with acid catalysis, of from 2 to 10 and preferably from 2.5 to 6 moles of glycidol per mole of alcohol or of alpha-diol containing from 10 to 14 carbon atoms at a temperature of from 50° to 120° C., the glycidol being added slowly to the alcohol or to the alpha-diol.

Among these compounds, the one obtained by condensation of monochlorohydrin (2.5 moles) in the presence of soda on 1,2-dodecanediol is particularly preferred.

These compounds are prepared according to the process described in French patent no. 72-40822 (2,169,787), the disclosure of which is herein incorporated by reference.

(5) Poly(hydroxypropylether) compounds prepared by poly-addition of glycerol monochlorohydrin on a polyhydroxylated organic compound in the presence of a strong base, by proportional elimination of the water by distallation.

These compounds are described more particularly in the French patent no. 84-19267 (2,574,786), the disclosure of which is herein incorporated by reference.

When the compositions according to the invention contain at least one surface-active agent, it is generally present at a concentration of between 0.5 and 10% by weight and preferably between 2 and 6% by weight relative to the total weight of the composition.

The reducing compositions are essentially aqueous and are in the form of a lotion, viscous or non-viscous, a cream or a gel. The pH of these compositions varies between 5 and 10 and preferably between 6.5 and 9.5.

One can use as acidifying agent an acid such as hydrochloric acid, phosphoric aid or citric acid, and as alkalinizing agent a compound chosen from among ammonia, mono-, di- or triethanolamine, and alkaline or ammonium carbonates or bicarbonates.

The reducing compositions according to the invention can also include various conventional cosmetic additives used in hair perms such as, for example, a softening agent, an opacifying agent, a sequestering agent, a treating agent, a perfume and/or a coloring agent.

This invention also has as its object a process for waving the hair in which one applies a reducing composition such as defined above to moistened hair wound previously onto rollers 4 to 20 mm in diameter. The composition may be applied as the hair is wound; one then allows the reducing composition to act for a time of from 5 to 60 min., preferably from 5 to 30 min.; then one rinses abundantly, after which one applies to the wound hair an oxidizing composition enabling the disulfide bonds of the keratin to be reformed, for a setting time of from 2 to 10 min. After having removed the rollers, one rinses the hair thoroughly. This oxidation step can be realized by allowing the oxygen of the air to act.

The oxidation or oxidizing composition is of the commonly used type and contains as oxidizing agent, for example, hydrogen peroxide, an alkaline bromate a per-salt a polythionate or a mixture of an alkaline bromate and a per-salt.

The concentration of hydrogen peroxide can vary from 1 to 10 volumes (i.e., the number of volumes of oxygen which 100 cm$^3$ of the solution will give on decomposition), but preferably is 8 volumes, the concentration of alkaline bromate is from 1 to 12% by weight and that of per-salt is from 0.1 to 15% by weight relative to the total weight of the oxidizing compostion.

The pH of the oxidizing composition can vary between 2 and 8, but preferably between 3 and 6.

The oxygenated water can be stabilized by, for example, phenacetin, acetanilide, mono- or trisodium phosphate, or 8-hydroxyquinoline sulfate.

The oxidation can be performed immediately or can be delayed.

The oxidizing compositions can also contain alkalinizing or acidifying agents, preservative agents, sequestering agents, opacifying agents and potentially a cationic copolymer such as those defined above for the reducing composition.

This invention also has as its object a process for relaxing, uncurling or uncrimping the hair in which one applies to the hair a reducing composition according to the invention, then one subjects the hair to a mechanical deformation enabling it to be fixed in its new shape by means of a hair-smoothing operation with a wide-toothed comb, with the back of a comb or by hand. After a setting time of from 5 to 60 min., in particular from 5 to 30 min., one then proceeds with a new smoothing; then one rinses carefully and one applies the oxidizing or fixing composition which is allowed to act for about 2 to 10 min; then one rinses the hair thoroughly.

COMPARATIVE STUDIES

To demonstrate the good properties of the reducing compositions according to the invention, the following,

| Composition A: | |
|---|---|
| Cysteamine hydrochloride | 5 g |
| Copolymer of N-vinylpyrrolidone/dimethylaminoethyl methacrylate in 20%-by-weight solution sold by the GAF Company under the name "Copolymer 845" | 1 g |
| NH$_4$OH qs | pH = 9 |
| Water qsp | 100 g | was compared to reducing compositions identical to Composition A but in which the "Copolymer 845" was replaced by the same quantity of a different cationic polymer, these compositions being the following:

| | |
|---|---|
| Composition B: | "GAFQUAT 734" sold by the GAF Company (Copolymer of N-vinylpyrrolidone/quaternized dimethylaminoethyl methacrylate with MW = 100,000). |
| Composition C: | "GAFFIX VC 713" sold by the GAF Company (terpolymer of N-vinylpyrrolidone/vinyl caprolactam/dimethylaminoethyl methacrylate). |
| Composition D: | "MERQUAT 100" sold by the MERCK-CALGON company (USA) (homopolymer of dimethyldiallylammonium with MW < 100,000). |
| Composition E: | Cationic polymer as described in and prepared according to the U.S. Pat. No. 4,217,914, consisting of repeating units of the formula: |

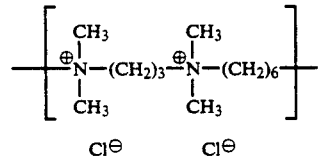

The compositions A to E as well as a control composition (composition not containing cationic copolymer) were subjected to two different tests: (i) the first involving the improvement in % of the curling efficiency according to the "pegboard" method whose technique, perfected by Kirby et al., has been described in "The Chemistry and Manufacture of Cosmetics", vol. IV, 2nd edition, Ed. G. de Navarre, p. 1211-1216, 1975, and (ii) the second involving the holding of the curls in the course of time by measurement of the falling of the curls, expressed in cm, in an atmosphere having a constant relative humidity of 90%.

The results according to these two tests, performed as double tests, are compiled in the following table:

| TESTS | CONTROL COMPOSITION | COMPOSITION A | COMPARISON COMPOSITIONS | | | |
|---|---|---|---|---|---|---|
| | | | B | C | D | E |
| % improvement of the curling efficiency | — | 15-20 | 0 | 0 | 0 | 0 |
| Holding of the curls in time, expressed by the falling of the waves in cm | | | | | | |
| After 1 h 30 min. | 3.3 | 1.2 | 2.3 | 3.5 | 3.4 | 4 |
| After 4 days | 5.5 | 2 | 5.4 | 5 | 5.4 | 6 |

According to these results it can be ascertained that Composition A according to the invention leads to a relative improvement of the curling efficiency of from 15 to 20% relative to the control composition. The other Compositions, B to E, do not lead to any improvement of the curling efficiency of the perm. Moreover, as concerns the holding of the curls in time, it is clearly superior for Composition A than for compositions B to E, both after 1 h 30 min. and after 4 days.

By way of illustration and without any limiting nature, several examples of reducing compositions according to the invention and of processes for their implementation will now be given.

EXAMPLES OF COMPOSITIONS

Example 1

One realizes a permanent wave of the hair by applying to all the hair the following reducing composition:

| | |
|---|---|
| Cysteamine hydrochloride | 4 g |
| Copolymer of N-vinylpyrrolidone/dimethylaminoethyl methacrylate in 20%-by-weight aqueous solution sold by the GAF Company under the name "Copolymer 845" | 0.5 g |
| Cocoamidopropyl-betaine sold by the GOLDSCHMIDT company under the name "Tégobétaine HS" | 2 g |
| Ammonia qs | pH = 9.2 |
| Coloring agent qs | |
| Perfume qs | |
| Water qsp | 100 g |

One then winds the hair onto rollers; then one allows the composition to act for a time of from 10 to 20 min., depending on the nature of the hair.

After rinsing with water, one then applies to the reduced hair the following oxidizing composition:

| | |
|---|---|
| Sodium bromate | 8 g |
| Mono- and trisodium phosphate | 0.8 g |
| Triethanolamine qs | pH = 7.5 |
| Perfume qs | |
| Coloring agent qs | |
| Water qsp | 100 g |

One allows the oxidizing composition to act for a time of from 10 to 15 min., rinses the hair with water and then removes the rollers and proceeds to a drying.

The hair exhibits and excellent holding of the curls in the course of time.

According to the same operating method as that described in Example 1 above, permanent waves of the hair have also been realized by means of the following reducing and oxidizing compositions:

Example 2

| Reducing composition: | |
|---|---|
| Cysteamine hydrochloride | 8 g |
| Copolymer of N-vinylpyrrolidone/dimethylaminoethyl methacrylate in 20%-by-weight aqueous solution sold by the GAF Company under the name "Copolymer 845" | 2 g |
| Nonionic poly(hydroxypropylether) surface-active agent prepared by condensation, with alkaline catalysis, of 3.5 moles of glycidol on a mixture of alpha-diols having from 10 to 14 carbon atoms according to the process described in FR patent no. 71-17206 (2,091,516) | 3 g |
| Monoethanolamine qs | pH = 9.0 |
| Perfume qs | |
| Coloring agent qs | |
| Water qsp | 100 g |

One allows the reducing composition to act for a time of from 10 to 20 min.

| Oxidizing composition: | |
|---|---|
| Hydrogen peroxide in aqueous solution at 200 volumes | 4.8 g |
| Stabilizers (8-hydroxyquinoline sulfate - phenacetin) | 0.05 g |
| Citric acid qs | pH = 3.0 |
| Perfume qs | |
| Coloring agent qs | |
| Water qsp | 100 g |

One allows the oxidizing agent to act for 10 min.

Example 3

| Reducing composition: | |
|---|---|
| Cysteamine hydrochloride | 10 g |
| Copolymer of N-vinylpyrrolidone/dimethylaminoethyl methacrylate in 50%-by weight solution in ethanol sold by the GAF Company under the name "Copolymer 958" | 1 g |
| Nonionic poly(hydroxypropylether) surface-active agent prepared by condensation, with alkaline catalysis, of 3.5 moles of glycidol on a mixture of alpha-diols having from 11 to 14 carbon atoms according to the process described in FR patent no. 71-17206 (2,091,516) | 4 g |
| Ammonia qs | pH = 8.5 |
| Coloring agent qs | |
| Perfume qs | |
| Water qsp | 100 g |

| Oxidizing composition: | |
|---|---|
| Hydrogen peroxide in aqueous solution at 200 volumes | 4.8 g |
| Stabilizers (8-hydroxyquinoline sulfate - phenacetin) | 0.05 g |
| Citric acid qs | pH = 3.0 |
| Perfume qs | |
| Coloring agent qs | |
| Water qsp | 100 g |

One allows the oxidizing agent to act for 10 min.

Example 4

| Reducing composition: | |
|---|---|
| Cysteamine hydrochloride | 5 g |
| Copolymer of N-vinylpyrrolidone/dimethylaminoethyl methacrylate in 20%-by-weight aqueous solution sold by the GAF Company under the name "Copolymer 937" | 2 g |
| Cocoamidopropyl-betaine sold by the GOLDSCHMIDT company under the name "Tégobpe,acu/e/ taine HS" | 2 g |
| Ammonia qsp | pH = 9.0 |
| Coloring agent qs | |
| Perfume, preservative qs | |
| Water qsp | 100 g |

| Oxidizing composition: | |
|---|---|
| Hydrogen peroxide in aqueous solution at 200 volumes | 4.8 g |
| Stabilizers (8-hydroxyquinoline sulfate - phenacetin) | 0.05 g |
| Nitric acid qsp | pH = 3.0 |
| Perfume qs | |
| Coloring agent qs | |
| Water qsp | 100 g |

One allows the oxidizing agent to act for 10 min.

Example 5

| Reducing composition: | |
|---|---|
| Cysteamine hydrochloride | 6 g |
| Cysteine | 3 g |
| Copolymer of N-vinylpyrrolidone/dimethylaminoethyl methacrylate in 20%-by-weight aqueous solution sold by the GAF Company under the name "Copolymer 845" | 1 g |
| Nonionic poly(hydroxypropylether) surface-active agent prepared by condensation, with alkaline catalysis, of 3.5 moles of glycidol on a mixture of alpha-diols having from 10 to 14 carbon atoms according to the process described in FR patent no. 71-17206 (2,091,516) | 2 g |
| Ammonia qsp | pH = 8.5 |
| Perfume qs | |
| Coloring agent, preservative, qs | |
| Water qsp | 100 g |

One allows the reducing composition to act for a time of from 10 to 20 min.

| Oxidizing composition: | |
|---|---|
| Hydrogen peroxide in aqueous solution at 200 volumes | 4.8 g |
| Stabilizers (8-hydroxyquinoline sulfate - phenacetin) | 0.05 g |
| Citric acid qs | pH = 3.0 |
| Perfume qs | |
| Coloring agent qs | |
| Water qsp | 100 g |

One allows the oxidizing agent to act for 10 min.

Example 6

| Reducing composition: | |
|---|---|
| N-acetylcysteamine | 8 g |
| Copolymer of N-vinylpyrrolidone/dimethylaminoethyl methacrylate in 20%-by-weight aqueous solution sold by the GAF Company under the name "Copolymer 845" | 1 g |
| Cocoamidopropyl-betaine sold by the GOLDSCHMIDT company under the name "Tégobétaine HS" | 3 g |
| Monoethanolamine qs | pH = 7.0 |
| Coloring agent qs | |
| Perfume qs | |
| Water qsp | 100 g |

| Oxidizing composition: | |
|---|---|
| Hydrogen peroxide in aqueous solution at 200 volumes | 4.8 g |
| Stabilizers (8-hydroxyquinoline sulfate - phenacetin) | 0.05 g |
| Citric acid qsp | pH = 3.0 |
| Perfume qs | |
| Coloring agent qs | |
| Water qsp | 100 g |

Example 7

| Reducing composition: | |
|---|---|
| N-acetylcysteamine | 6 g |
| Copolymer of N-vinylpyrrolidone/dimethylaminoethyl methacrylate in 20%-by-weight aqueous solution sold by the GAF Company under the name "Copolymer 845" | 0.05 g |
| Nonionic poly(hydroxypropylether) surface-active agent prepared by condensation, with alkaline catalysis, of 3.5 moles of glycidol on a mixture of alpha-diols having from 11 to 14 carbon atoms accoridng to the process described in FR patent no. 71-17206 (2,091,516) | 2 g |
| Ammonia qs | pH = 9.0 |
| Perfume qs | |
| Coloring agent qs | |
| Water qsp | 100 g |

One allows the reducing composition to act for a time of from 10 to 20 min.

| Oxidizing composition: | |
|---|---|
| Hydrogen peroxide in aqueous solution at 200 volumes | 4.8 g |
| Stabilizers (8-hydroxyquinoline sulfate - phenacetin) | 0.05 g |
| Citric acid qs | pH = 3.0 |
| Perfume qs | |
| Coloring agent qs | |
| Water qsp | 100 g |

One allows the oxidizing agent to act for 10 min.

Example 8

| Reducing composition: | |
|---|---|
| N-acetylcysteamine | 6 g |
| N-acetylcysteine | 6 g |
| Copolymer of N-vinylpyrrolidone/dimethylaminoethyl methacrylate in 20%-by-weight aqueous solution sold by the GAF Company under the name "Copolymer 845" | 0.8 g |
| Nonionic poly(hydroxypropylether) surface-active agent prepared by condensation, with alkaline catalysis, of 3.5 moles of glycidol on a mixture of alpha-diols having from 11 to 14 carbon atoms according to the process described in FR patent no. 71-17206 (2,091,516) | 4 g |
| Ammonia qs | pH = 9.0 |
| Coloring agent qs | |
| Perfume qs | |
| Water qsp | 100 g |

One allows the reducing composition to act for a time of from 10 to 20 min.

| Oxidizing composition: | |
|---|---|
| Hydrogen peroxide in aqueous solution at 200 volumes | 4.8 g |
| Stabilizers (8-hydroxyquinoline sulfate - phenacetin) | 0.05 g |
| Citric acid qs | pH = 3.0 |
| Perfume qs | |
| Coloring agent qs | |
| Water qsp | 100 g |

One allows the oxidizing agent to act for 10 min.

Example 9

| Reducing composition: | |
|---|---|
| Cysteamine hydrochloride | 12 g |
| N-acetylcysteine | 2 g |
| Copolymer of N-vinylpyrrolidone/dimethylaminoethyl methacrylate in 20%-by-weight aqueous solution sold | 1.5 g |

-continued

| Reducing composition: | |
|---|---|
| by the GAF Company under the name "Copolymer 845" | |
| Ammonia qsp | pH = 9.0 |
| Coloring agent qs | |
| Perfume qs | |
| Preservative qs | |
| Water qsp | 100 g |

| Oxidizing composition: | |
|---|---|
| Hydrogen peroxide in aqueous solution at 200 volumes | 4.8 g |
| Citric acid qsp | pH = 3.0 |
| Stabilizers qs | |
| Water qsp | 100 g |

Example 10

| Reducing composition: | |
|---|---|
| N-acetylcysteamine | 10 g |
| Cysteine | 2 g |
| Copolymer of N-vinylpyrrolidone/dimethylaminoethyl methacrylate in 20%-by-weight aqueous solution sold by the GAF Company under the name "Copolymer 845" | 0.4 g |
| Ammonia qsp | pH = 9.0 |
| Coloring agent qs | |
| Perfume qs | |
| Preservative qs | |
| Water qsp | 100 g |

| Oxidizing composition: | |
|---|---|
| Hydrogen peroxide in aqueous solution at 200 volumes | 4.8 g |
| Citric acid q.s.p. | pH = 3.0 |
| Stabilizers qs | |
| Water qsp | 100 g |

We claim:

1. A reducing composition for permanently deforming hair in the cold state comprising
   (1) a reducing agent wherein said reducing agent is present at a concentration of between 0.1 and 15% by weight and is selected from the group consisting of cysteamine, a cysteamine salt and N-acetylcysteamine; and
   (2) a cationic polymer wherein said cationic polymer is present at a concentration of between 0.1 and 3% by weight and said cationic polymer is a polymer of 45 to 99.5 mole % N-vinylpyrrolidone and 0.5 to 55 mole % non quaternized dialkyl ($C_1$14 $C_4$) aminoalkyl ($C_1$-$C_{18}$) acrylate or methacrylate.

2. A reducing composition according to claim 1, wherein said cysteamine salt is cysteamine hydrochloride.

3. A reducing composition according to claim 1, wherein the concentration of said reducing agent is between 3 and 8% by weight relative to the total weight of the reducing composition.

4. A reducing composition according to claim 1, wherein said cationic polymer is a copolymer of 80 to 99.5 mole-% N-vinylpyrrolidone and 0.5 to 20 mole-% dimethylaminoethyl methacrylate.

5. A reducing composition according to claim 1, wherein the active-substance concentration of said cationic polymer is between 0.5 and 2% by weight relative to the total weight of the reducing composition.

6. A reducing composition according to claim 1, wherein said reducing component further contains cysteine or N-acetylcysteine at a concentration of between 0.1 and 10% by weight relative to the total weight of the reducing composition.

7. A reducing composition according to claim 6, wherein the concentration of said cysteine or N-acetylcysteine is between 1.5 and 8% by weight relative to the total weight of the reducing composition.

8. A reducing composition according to claim 1, further comprising:
   (3) at least one surfactant selected from the group consisting of a nonionic surface-active agent, an anionic surface-active agent and an amphoteric surface-active agent.

9. A reducing composition according to claim 8, wherein said surfactant is a nonionic poly(hydroxypropylether) surface-active agent.

10. A reducing composition according to claim 8, wherein said surfactant is present at a concentration of between 0.5 and 10% by weight relative to the total weight of the reducing composition.

11. A reducing composition according to claim 10, wherein the concentration of said surfactant is between 2 and 6% by weight relative to the total weight of the reducing composition.

12. A reducing composition according to claim 1, wherein the reducing composition has a pH between 5 and 10.

13. A reducing composition according to claim 12, wherein the pH is between 6.5 and 9.5.

14. A reducing composition according to claim 1, further comprising:
   (3) at least one cosmetic additive selected from the group consisting of a softening agent, an opacifying agent, a sequestering agent, a treating agent, a perfume and a coloring agent.

15. A process for permanently deforming the hair, comprising the steps of:
   (1) applying a reducing composition to the hair thereby reducing disulfide bonds of keratin, wherein said reducing composition comprises
      (a) a reducing agent, selected from the group consisting of cysteamine, cysteamine salt and N-acetylcysteamine; and
      (b) a cationic polymer, of 45 to 99.5 mole % N-vinylpyrrolidone and 0.5 to 55 mole % nonquaternized dialkyl ($C_1$-$C_4$) aminoalkyl ($C_1$-$C_{18}$) acrylate or methacrylate; and then
   (2) applying an oxidizing composition to the hair thereby reforming said disulfide bonds.

16. A process according to claim 15, wherein step (1) includes moistening the hair, winding rollers 4 to 200 mm in diameter into the hair, and applying said reducing composition to the moistened hair for waving the hair.

17. A process according to claim 15, wherein step (1) includes applying said reducing composition to the hair and thereafter subjecting the hair to smoothing by means of a comb for uncurling or uncrimping the hair.

18. A process according to claim 15 wherein step (1) includes applying said reducing composition to the hair and allowing said reducing composition to act on the hair for a time between 5 and 60 minutes.

* * * * *